United States Patent [19]

Wright

[11] Patent Number: 4,812,214

[45] Date of Patent: Mar. 14, 1989

[54] METHOD OF COMBINING SILOXY GROUPS WITH KETENE-REACTIVE COMPOUNDS

[75] Inventor: Bradford B. Wright, North St. Paul, Minn.

[73] Assignee: Minnesota Mining & Manufacturing Company, St. Paul, Minn.

[21] Appl. No.: 101,589

[22] Filed: Sep. 28, 1987

[51] Int. Cl.$^4$ .............................................. B01J 19/08
[52] U.S. Cl. ........................... 204/157.74; 204/157.93; 522/130; 522/172; 556/436
[58] Field of Search ...................... 204/157.74, 157.93; 556/436; 522/130, 172; 525/105; 528/25

[56] References Cited

U.S. PATENT DOCUMENTS 4,302,563 11/1981 Vaughn .................................. 525/292
4,530,879 7/1985 Drahnak .......................... 204/157.74

Primary Examiner—John F. Niebling
Assistant Examiner—Ben C. Hsing
Attorney, Agent, or Firm—Tilton, Fallon, Lungmus & Chestnut

[57] ABSTRACT

A method of combining a siloxy group (—SiO—) with a ketene-reactive compound to form a siloxy-containing product comprises:

(a) subjecting a silyl diketone to photolysis under conditions effective for generating a siloxy ketene intermediate therefrom, said silyl diketone having the formula

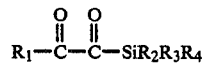

wherein Si is silicon, $R_1$ and $R_4$ are hydrocarbon groups containing from 1 to 18 carbons, and $R_2$ and $R_3$ are hydrocarbon groups containing from 1 to 6 carbons, said photolysis being carried out by irradiating said silyl diketone with light of a wavelength from 200 to 800 nm; and, thereafter, (b) contacting the generated siloxy ketene intermediate with a ketene-reactive compound under conditions effective for reaction therewith, said compound being selected from the group consisting of (i) a diene polymer containing a plurality of unsaturated carbon bonds, (ii) an alkylene or cycloalkylene compound containing at least one unsaturated linkage; and (iii) an aldehyde containing one or more aldehyde groups.

9 Claims, No Drawings

METHOD OF COMBINING SILOXY GROUPS WITH KETENE-REACTIVE COMPOUNDS

FIELD OF INVENTION

The field of this invention is ketene chemistry, including particularly the reactions of ketenes with aldehydes and olefinic compounds.

BACKGROUND OF INVENTION

Ketenes have been important intermediates in chemistry for many years, demonstrating a wide variety of applications. The ketene functionality

reacts readily with aldehydes to produce beta-lactones. Ketenes also react with thiazoles to produce antibiotics. Patai, "The Chemistry of Ketenes, Allenes, and Related Compounds" (1980); Isaacs (1976); and Borrmann, et al. (1969). Ketenes also react with the unsaturated linkages of olefinic compounds to form cyclobutanone groups. This reaction is described in U.S. Pat. No. 4,302,563 (1981) for increasing the adhesiveness of conjugated diene polymers.

There are several known methods for generation of ketenes, including the dehydrochlorination of acyl chlorides with tertiary amines, and the photolysis of diazo oxides. Brady, et al. (1967); and Meier, et al. (1975).

Methods for modification of the physical and/or chemical properties of compounds which can be formed from ketenes are of recognized importance. The siloxy group (—SiO—) would be a useful functionality for such modifications. However, as far as is known, there has been no report of a method for combining siloxy groups with ketene-reactive compounds. In fact, siloxy ketenes appear to be a novel class of compounds not previously known, although such ketenes would have interesting properties, being simultaneously a ketene and a silyl enol ether. It appears that the potential value of siloxy ketenes as synthetic intermediates has not previously been recognized.

As far as is known, the literature of photochemical reactions does not include any report of a photochemical reaction of silicon-containing diketones, such as the 1-silyl-1,2-diones. Background references on photochemistry include Brook (1973) *Intra-Science Chem. Rept.*, 7:131-138; and Bryce-Smith, "Photochemistry", Vol. 9, pages 320-335, and Vol. 10, pages 281-297.

SUMMARY OF INVENTION

This invention is based in part on the discovery that silicon-containing diketones, specifically 1-silyl-1,2-diones, can be converted by photolysis to siloxy ketene intermediates, which intermediates are reactive with the same classes of compounds as unsubstituted ketenes, thereby permitting siloxy groups to be introduced into the reaction products. This hitherto unknown photoreaction of silyl diketones has wide applicability. For example, the photoreaction can be employed to introduce siloxy-substituted cyclobutanone groups into olefinic compounds such as diene polymers. A further application is the photoreaction of 1-silyl-1,2-diones to produce siloxy-substituted beta-lactones.

Siloxy ketenes are prepared as a reaction intermediate from 1-silyl-1,2-diones by light irradiation. This photolysis process can be carried out easily and inexpensively. Siloxy ketene intermediates are highly active, reacting rapidly on contact with ketene-reactive compounds such as those having unsaturated carbon-to-carbon bonds and aldehyde groups. The ketene-reactive compound may be a diene or a polymer containing carbon-to-carbon double bond or olefinic linkages.

It is desirable but not essential to have ketene-reactive compounds present in the reaction mixture on the formation of the siloxy ketene intermediate. In applications such as adhesive coatings on substrates, the coating containing ketene reactive compounds can be applied with the unreacted silyl diketone therein. After application, the coating can be irradiated to produce, in situ, the siloxy ketene intermediate, which can react with the olefinic linkages to introduce siloxy cyclobutanone groups.

DETAILED DESCRIPTION

The novel photochemical reaction employed in the method of this invention is represented by the following equation:

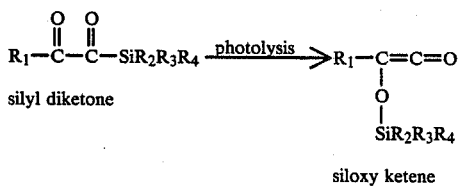

In the foregoing formulas, the "R" groups may be hydrocarbon groups, which may or may not be substituted by oxygen and nitrogen. The term "hydrocarbon group" is therefore used herein as a generic term. $R_1$ and $R_2$ can be hydrocarbon groups containing from 1 to 18 carbons, and $R_2$ and $R_3$ can be hydrocarbon groups containing from 1 to 6 carbons. The preferred silyl diketones and the siloxy ketenes formed therefrom contain two single carbon "R" groups together with two short chain alkyl groups. For example, $R_2$ and $R_3$ can be $CH_3$, while $R_1$ and $R_4$ can be alkyl groups containing from 1 to 6 carbons. Si designates silicon.

The silyl diketones are 1-silyl-1,2-diones. They can be produced as starting materials by previously known methods. Such methods are described by Reich et al. (1982); Reich et al. (1983); and Bulman-Page (1986). The method of Reich et al. is described in Example I.

Representative of the silyl diketones or 1-silyl-1,2-diones are compounds Ia and Ib below:

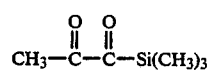

The silyl diketone reactant can be used without solvent or it can be dissolved in a suitable inert solvent which also contains the ketene-reactive compound. The inert solvent should be one which does not act or degrade under conditions of the reaction, and should solubilize or be miscible with the siloxy ketene and the ketene-reactive compound. The resultant reaction mixture is then irradiated with light. Daylight or artificially generated visible and/or ultraviolet light can be used. Photolysis can be carried out by irradiation with light at wavelengths of from 200 to 800 nm. Preferably, however, irradiation is with visible light, such as at wavelengths of about 400 to 600 nm. High energy irradiation is not required. The required light energy may be generated by conventional visible and/or ultraviolet light sources, including incandescent and fluorescent light sources.

The described photolysis reaction can be carried out at ordinary ambient temperatures, such as at temperatures of 20–30° C. More broadly, temperatures from −20 to 50° C. are useable. As long as the reaction mixture is a liquid or is above the glass transition temperature of the mixture, heating of the mixture to higher temperatures than those indicated is not needed. Further, excessive heating may promote formation of other products; and, in the case of polymers, excessive heating can induce cross-linking. The range of molecular weights of the olefin-containing polymer is not critical as long as the reaction can be carried out above the glass transition temperature of the polymer. Molecular weights of from 200 to 2 million for the resultant polymers can be achieved.

In other embodiments, the ketene reactive compound may be a liquid which itself provides the liquid phase. In those embodiments, the silyl diketone and the resultant generated siloxy ketene should be soluble in the liquid ketene-reactive compound.

If inert solvent is used, hydrocarbon solvents are preferred, such as benzene, toluene, xylene, etc. However, other inert solvents can be used such as chlorinated hydrocarbon solvents like trichloroethane, ethylene dichloride, etc.

In still other embodiments, the reaction may be carried out in a viscous phase (i.e., above the glass transition phase), such as in the adhesive coating after its application to a substrate. In those embodiments, the silyl diketone is premixed with the adhesive composition. For example, the adhesive composition may include one or more conjugated diene polymers. The mix is applied to the substrate and thereafter irradiated to produce in situ the siloxy-ketene intermediate, which will react with the conjugated diene linkages to form siloxy cyclobutanone groups along the polymer chains of the adhesive composition. Such adhesive formulations may contain solvents which can be present on initial application of the adhesive to the substrate and during irradiation of the coating. After the in situ reaction, the coating can be dried to remove the solvent.

The reaction mixture is preferably kept essentially free of oxygen. This has reference to the liquid phase itself, but it may be preferable to employ an oxygen-free atmosphere in contact with the liquid phase. If so, a nitrogen atmosphere can be used. The presence of trace amounts of oxygen in the liquid mixture can be tolerated so long as the primary reaction is between the ketene intermediate and the ketene-reactive compound.

Amounts of the silyl diketone employed in relation to the ketone-reactive compound can vary widely. The maximum amounts which can be reacted are determinable in relation to the number of unsaturated linkages (electron-rich C—C double bonds) and/or the number of aldehyde groups, a 1:1 molar ratio being the maximum. To assure completion of reaction with the unsaturated linkages with the aldehyde groups, however, an excess of the silyl diketone can be employed. On the other hand, it may be desirable to react the siloxy ketene intermediate with only a portion of the unsaturated linkages, or with only a portion of the aldehyde groups. (By electron-rich C—C double bond is meant any alkene which bears substituents having a combined Hammett sigma value of less than zero. By "alkene" is meant any compound or polymer containing at least one olefinic double bond.)

Elastomeric diene polymers or copolymers prepared from conjugated diene monomers are an especially important class of the ketene-reactive compounds which can be used in the method of this invention. Such polymers and copolymers include those prepared from 1,3-butadiene, isoprene, chloroprene, 2-phenyl-1,3-butadiene, 1,3-pentadiene, 2-vinycyclohexene, 2-chloro-1,3-pentadiene, and mixtures of such monomers. The resulting polybutadienes, polyisoprenes, polypentadienes, etc. include at least one and preferably a plurality of reactive unsaturated linkages (the conjugated diene functionalities). These are reactive with the siloxy ketene intermediates. Siloxy-substituted cyclobutanone groups can be readily introduced into the conjugated diene polymers at the points of unsaturation in the polymer chains.

The siloxy-containing cyclobutanone groups which result from the reaction of the siloxy ketene with diene polymers or other olefinic compounds can be represented by the following formula:

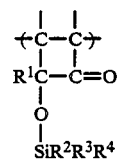

IV

The values for "R" should be understood as having the same meanings as previously described for the silyl diketones and the siloxy ketenes.

Similarly, siloxy-substituted cyclobutanone groups can be incorporated in alkylene or cycloalkylene compounds. The alkylene compounds may be substituted, such as with oxygen or nitrogen, and should provide one or more carbon-to-carbon unsaturated linkages. For example, aliphatic alkenes containing from 2 to 20 carbon atoms can be used. Similarly, cycloalkylene compounds can be employed. Examples of alkenes are ethene, propene, butene, pentene, etc. Examples of cycloalkylenes are cyclohexene, 2,3-dihydropyran, cyclopentadiene, etc.

A third class of the ketene-reactive compounds is the aldehydes. These may include one or more aldehyde groups. Representative compounds are acetaldehyde, benzaldehyde, and glutaraldehyde. The aldehydes typically may contain from 2 to 20 carbons.

As can be seen from the foregoing description, the siloxy ketene intermediates are reactive with olefinic linkages, particularly with conjugated diene groups, and also with aldehyde groups. The method of this invention is therefore broadly applicable to these classes of compounds. It will also be apparent to those skilled in the art that the siloxy ketenes can be generated first and the resultant reactive intermediate can be treated with a reactant thereafter, that is, as a two-part system.

The method of this invention and the novel products produced thereby are further illustrated by the following examples. The siloxy-ketenes generated reacted with substrates that are identified spectroscopically and are shown to react with substrates in a manner typical of ketenes. The 1-silyl-1,2-diones in siloxy ketenes, as well as products from the reaction of the latter with ketene reactive substrates, were monitored by one or a combination of IR, NMR, and mass spectroscopies.

EXAMPLE I

The 1-silyl-1,2-diones Ia and Ib were synthesized by the method of Reich et al. (1983).

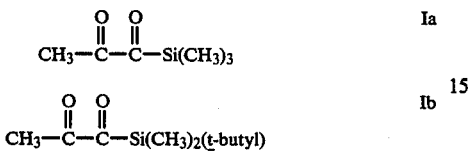

Briefly, the diones were prepared as follows: The synthesis of 1-silyl-1,2-diones was accomplished by the following procedure described by Reich et al. (1982). Propargyl alcohol was treated with ethyl vinyl ether in the presence of p-toluenesulfonic acid. The resulting protected alcohol was isomerized to the allenol ether by heating in the presence of catalytic amounts of potassium t-butoxide. The allenol ether was then silylated at -90° in tetrahydrofuran by treatment with n-butyllithium and the corresponding chlorosilane. Finally, the preparation of the 1-silyl-1,2-dione was achieved by oxidation of the silylated allenol ether with m-chloroperoxybenzoic acid in dichloromethane solvent. The material was purified by distillation and/or gas chromatography.

Purification of compounds Ia and Ib was accomplished by preparative gas chromatography on a 6'×¼" 10% OV-101 on 60/80 mesh WHP packed column. Photolyses on a preparative scale were performed as follows:

In a 13 mm OD Kimax ™ brand test tube was placed a solution containing 50–100 mg of freshly purified Ia, 3 ml of a hydrocarbon solvent, and 2 ml of the alkene to be used as coreactant. The tube was sealed with a screw cap and a Teflon-lined rubber septum. The sample was then deoxygenated by purging with dry nitrogen for 15 minutes in the dark. The tube and its contents were then irradiated (at a distance of about 15 cm., about six inches) using a Kodak carousel 5200 slide projector (Eastman Kodak, Rochester, N.Y.) with a cutoff filter (Ealing 475 nm filter, Ealing Corp., South Natick, Mass.) inserted into the slide apperture of the projector. Photolysis was stopped when no purple color could be visually detected. The solution was clear and colorless at this point and was concentrated on a rotary evaporator. The residue was purified by preparative gas chromatography using the same column as before.

EXAMPLE II

The following example describes the preparation of a siloxycyclobutanone from compound Ia and cyclohexene.

Ia was photolyzed in the presence of commercial cyclohexene as described in Example I. The resulting colorless liquid was isolated by gas chromatography.

EXAMPLE III

The following example describes the preparation of a siloxycyclobutanone from compound Ia and 1-pentene.

Ia was photolyzed in the presence of commercial 1-pentene (98+%) as described in Example I. The resulting colorless liquid was isolated by gas chromatography.

EXAMPLE IV

The following example describes the preparation of a siloxycyclobutanone from Compound Ia and 2,3-dihydropyran.

Ia was photolyzed in the presence of commercial 2,3dihydropyran as described in Example I. The resulting colorless liquid was isolated by gas chromatography.

EXAMPLE V

The following example describes the preparation of a siloxycyclobutanone from Compound Ia and cyclopentadiene.

Ia was photolyzed in the presence of freshly distilled commercial cyclopentadiene as describd in Example I. The resulting colorless liquid was isolated by gas chromatography.

EXAMPLE VI

The following example describes the preparation of 2-oxetanones by photolysis of Ia in pentane solution in the absence of coreactants.

Photolysis of Ia as described in Example I in the absence of added electron-rich alkenes resulted in the formation of complicated product mixtures (in contrast to the simple mixtures when electron-rich alkenes were present), which were examined by gas chromatography/mass spectroscopy (GC/MS), IR, and NMR.

EXAMPLE VII

The following example describes the preparation of 2-oxetanones by photolysis of compound Ia in pentane solution in the presence of acetaldehyde and benzaldehyde respectively.

Ia was photolyzed in the presence of freshly distilled acetaldehyde or benzaldehyde respectively as described in Example I. The product was identified by IR.

EXAMPLE VIII

The following example describes the photolysis of compound Ia in the presence of oxygen (air).

Irradiation of Ia in commercial cyclohexane as described in Example I while purging the solution with air resulted in the clean formation of a clear colorless liquid which rapidly hydrolyzed in the laboratory environment. This material was identified as trimethylsilyl pyruvate.

EXAMPLE IX

The following example describes the spectroscopic observation of siloxyketene (compound IIa) during photolysis of compound Ia.

Observation of the ketene carbonyl stretch in IIa and was accomplished by preparation of mulls containing Ia with Nujol brand heavy mineral oil (5 drops/10 ul Ia). The mull was placed between sodium chloride salt plates and the assembly was placed into the sample compartment of a Perkin-Elmer (Norwalk, Conn.) model 983 scanning infrared spectrometer. After recording a baseline spectrum light was introduced from the Kodak slide projector/filter apparatus described in Example I by manually aiming the beam into the spectrometer. Subsequent scanning with the light on showed an absorption band indicating the presence of a ketene. Removal of the light source resulted in a rapid decline of the signal intensity. By monitoring the absorbance at 2105 cm$^{-1}$ as a function of time it was possible to determine that the decay followed first order kinetics over >90% of the decay, and was complete in 15–30 seconds. The experiment was reproduced using Vaseline brand petroleum jelly and two Fluorolubes (Hooker, 160 and 1200 wt., Hooker Chemical Co., Houston, Tex.), with comparable results.

EXAMPLE X

The following example describes the spectroscopic observation of siloxyketene IIb during photolysis of compound Ib.

Observation of the ketene carbonyl stretch in IIb was accomplished by preparation of mulls containing Ib with Nujol brand heavy mineral oil (5 drops/ 10 μl Ib). The mull was placed between sodium chloride salt plates and the assembly was placed into the sample compartment of a Perkin-Elmer model 983 scanning infrared spectrometer. After recording a baseline spectrum light was introduced from the Kodak slide projector/filter apparatus described in Example I by manually aiming the beam into the spectrometer. Subsequent scanning with the light on showed an absorption band consistent with a ketene. Removal of the light source resulted in a slow decline of the signal intensity. Greater than 300 seconds were required for complete signal decay to occur at room temperature.

EXAMPLE XI

The following example describes a typical preparation of siloxycyclobutanone modified polydiene polymer.

Polybutadiene (1.00 g, Aldrich Chemical Co., Milwaukee, Wis., #18,138-2, cis and trans) was dissolved in 100 ml commercial cyclopentane. A 5 ml aliquot was removed and added to first and second pyrex test tubes, each fitted with a septum cap. The required amount of silyl diketone Ia and Ib was added to the first and second tubes respectively. Each tube was purged with dry nitrogen for 20 minutes in the dark and then irradiated; irradiation was accomplished using a Kodak Carousel 5200 slide projector using a GE FHS 300W 82V projection lamp. An Ealing 475 nm cutoff filter was inserted into the projector to ensure irradiation of only the long wave absorption band at 530 nm. The respective tube was irradiated until no pink color remained in the solution (about 10 min). Each resultant mixture was then transferred to a respective flask and attached to high vacuum at room temperature for 6 hours to remove volatile material; it is important and known in the art that if volatile materials remain in the polymer, erroneous measurements of peel adhesion may result. The respective material was analyzed or redissolved for coating experiments.

Coatings from 2% wt/vol solutions of the modified cyclobutanone containing polymer in cyclopentane were made on to polyvinylidene chloride-primed polyethylene terephthalate film (3M film, 3M, St. Paul, Minn.) as a substrate using a number 22 wire wrapped rod and the resultant layered structure was allowed to air dry 15 minutes before being placed in a vacuum oven at 60° for 4 hours to dry.

Peel adhesion measurements were made on an Instrumentors slip/peel tester model 3M90 (Cleveland, Ohio) using a 2 lb weight and a 90 in/min peel rate. Scotch Brand ™ Magic ™ Tape (¾", 3M, St. Paul, Minn.) was used as the adhesive substrate removed from polymer coated surfaces.

Experiments were performed on all samples to ensure that material transfer had not occurred during the peeling process, or that tackiness was not due to insufficient drying of the sample.

Results from siloxycyclobutanone-modified polydienes are described in Table I. Generally, an increase in the observed peel adhesion was found as compared to control polydienes. Further a correlation between the extent of adhesion increase and the extent of siloxycyclobutanone formation can be seen; the higher the amount of siloxycyclobutanone formation, the higher the peel adhesion measured.

In the case of polyisoprene similar results were obtained. Measurement of the peel adhesion of polyisoprene (control) was not possible since this material peeled off the polyvinylidene chloride substrate during testing. In contrast, once the polymer was modified to provide a siloxycyclobutanonecontaining polymer of this invention, it maintained adhesion to the substrate indicating both an increase in adhesion, and that this process is useful in priming surfaces.

TABLE I

Peel Adhesion Values for Modified Polydiene Polymers and Reference Materials.

| Polymer | Substrate | Peel Adhesion oz/in | Notes |
|---|---|---|---|
| PBD$^a$ | PVC$^b$ | 1.0 | |
| PBD$^a$ | polyester | 0.6 | |
| — | pyrex | 23.1 | |
| — | polyester | 18.2 | |
| — | PVC$^b$ | 12.9 | |
| A | PVC$^b$ | 28.5 | |
| A | polyester | 27.6 | |
| B | PVC$^b$ | 18.3 | |
| C | PVC$^b$ | 28.3 | |
| D | PVC$^b$ | 29.3 | |
| E | PVC$^b$ | 24.3 | |
| F | PVC$^b$ | — | peeled off |
| F | PVC$^b$ | 32.8 | air dried |
| F | PVC$^b$ | 40.1 | air dried |
| G | PVC$^b$ | 6.1 | |
| H | PVC$^b$ | 10.5 | |
| I | PVC$^b$ | 16.6 | |

A = 0.72 g solution containing Ia (about 50% by GC)/1.0 g PBD
B = 9 mg Ia/110 mg PBD
C = 36 mg Ib/110 mg PBD
D = 90 mg Ia/110 mg PBD
E = 45 mg Ia/110 mg PBD
F = 90 mg Ia/110 mg PIP$^c$
G = 5 mg Ia/100 mg c-PBD$^d$
H = 10 mg Ia/100 mg c-PBD$^d$
I = 20 mg Ia/100 mg c-PBD$^d$
$^a$PBD = polybutadiene (Aldrich, #18, 138-2, cis and trans)
$^b$polyester film primed with polyvinylidene chloride (PVC)
$^c$PIP = polyisoprene, (Aldrich, #18, 216-8, trans)
$^d$c-PBD = polybutadiene (Aldrich, #18, 137-4, cis)

REFERENCES

Borrmann, D.; Wegler, R. (1969), Chem. Ber. 102, 64.
Brady, W. T.; Waters, O. H. (1967), J. Org. Chem. 32, 3703.
Brook (1973), Intra-Science Chem. Rept. 7:131–138.
Bryce-Smith, "Photochemistry" (The Chemical Society), Vol. 9 (1976–1977), pages 320–335; and Vol. 10 (1977–1978), pages 281–297.
Isaacs, N. S. (1976), Chem. Soc. Rev., 5, 181.
Meier, H., Zeller, K.-P, (1975), Angew. Chem. Internat. Ed. Engl. 14, 32.

Patai, Saul (Ed.), "The Chemistry of Ketenes, Allenes, and Related Compounds", Part 1 (John Wiley and Sons, New York, 1980), Chapt. 7, pages 223–277.

Reich, H. J., and Kelly, M. J., *J. Am. Chem. Soc.* 1982, 104, 1119.

Reich, H. J., Kelly, M. J., Olson, R. O., and Holtan, R. C., *Tetrahedron* 1983, 39, 949.

Bulman Page, P. C., and Rosenthal, S., *Tetrahedron Lett.* 1986, 27, 2527.

Vaughn, W. L., U.S. Pat. No. 4,302,563.

I claim:

1. The method of combining a siloxy group (-SiO-) with a ketene-reactive compound to form a siloxy-containing product comprising:
   (a) subjecting a silyl diketone to photolysis under conditions effective for generating a siloxy ketene intermediate therefrom, said silyl diketone having the formula

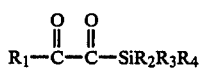

wherein Si is silicon, $R_1$ and $R_4$ are hydrocarbon groups containing from 1 to 18 carbons, and $R_2$ and $R_3$ are hydrocarbon groups containing from 1 to 6 carbons, said photolysis being carried out by irradiating said silyl diketone with light of a wavelength from 200 to 800 nm; and, thereafter,
   (b) contacting the generated siloxy ketene intermediate with a ketene-reactive compound under conditions effective for reaction therewith, said compound being selected from the group consisting of (i) a diene polymer containing a plurality of unsaturated carbon bonds, (ii) an alkylene or cycloalkylene compound containing at least one unsaturated linkage; and (iii) an aldehyde containing one or more aldehyde groups.

2. The method of claim 1 in which said ketene-reactive compound is diene polymer containing a plurality of unsaturated carbon bonds.

3. The method of claim 1 in which said ketene-reactive compound is alkylene or cycloalkylene compound containing at least one unsaturated linkage.

4. The method of claim 1 in which said ketene-reactive compound is an aldehyde containing one or more aldehyde groups.

5. The method according to claim 1 wherein said step (a) takes place in the absence of oxygen.

6. The method of introducing a siloxy-substituted cyclobutanone group into a conjugated diene polymer or copolymer, comprising
   (a) subjecting a silyl diketone to photolysis under conditions effective for generating a siloxy ketene intermediate therefrom, said silyl diketone having the formula

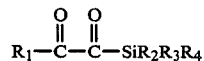

wherein Si is silicon, $R_1$ and $R_4$ are hydrocarbon groups containing 1 to 6 carbons, and $R_2$ and $R_3$ are methyl groups, said photolysis being carried out by irradiating said silyl diketone with light of a wavelength from 200 to 800 nm; and
   (b) concurrently with the generation of the siloxy ketene intermediate, contacting it with a conjugated diene polymer or copolymer containing a plurality of diene groups under conditions effective for reaction therewith.

7. The method of introducing a siloxy-substituted cyclobutanone group into alkylene compound, comprising:
   (a) subjecting a silyl diketone to photolysis under conditions effective for generating a siloxy ketene intermediate therefrom, said silyl diketone having the formula

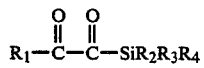

wherein Si is silicon, $R_1$ and $R_4$ are hydrocarbon groups containing from 1 to 18 carbons, and $R_2$ and $R_3$ are hydrocarbon groups containing from 1 to 6 carbons, said photolysis being carried out by irradiating said silyl diketone with light of a wavelength from 200 to 800 nm; and
   (b) concurrently with the generation of the siloxy ketene intermediate contacting it with an alkylene compound under conditions effective for reaction therewith, said compound being selected from the group consisting of aliphatic alkenes containing from 2 to 20 carbons and cycloalkenes containing from 3 to 20 carbons.

8. The method of preparing beta-lactone compounds containing a siloxy group (-SiO-) comprising:
   (a) subjecting a silyl diketone to photolysis under conditions effective for generating a siloxy ketene intermediate therefrom, said silyl diketone having the formula

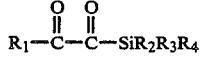

wherein Si is silicon, $R_1$ and $R_4$ are hydrocarbon groups containing from 1 to 18 carbons, and $R_2$ and $R_3$ are hydrocarbon groups containing from 1 to 6 carbons, said photolysis being carried out by irradiating said silyl diketone with light of a wavelength from 200 to 800 nm; and
   (b) concurrently with the generation of the siloxy ketene intermediate contacting it with aldehyde compounds containing from 1 to 2 aldehyde groups and from 2 to 20 carbons under conditions effective for reaction therewith.

9. The method of claim 1, 6, 7, or 8 in which said irradiation is carried out with light at a wavelength of from 400 to 600 nm.